(12) United States Patent
Hashimoto et al.

(10) Patent No.: US 11,083,376 B2
(45) Date of Patent: Aug. 10, 2021

(54) PHOTOACOUSTIC MEASUREMENT DEVICE AND SIGNAL PROCESSING METHOD OF PHOTOACOUSTIC MEASUREMENT DEVICE

(71) Applicant: FUJIFILM Corporation, Tokyo (JP)

(72) Inventors: Atsushi Hashimoto, Kanagawa (JP); Kaku Irisawa, Kanagawa (JP); Atsushi Osawa, Kanagawa (JP); Tomoki Inoue, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 480 days.

(21) Appl. No.: 15/901,041

(22) Filed: Feb. 21, 2018

(65) Prior Publication Data

US 2018/0177407 A1 Jun. 28, 2018

Related U.S. Application Data

(63) Continuation of application No. PCT/JP2016/004307, filed on Sep. 21, 2016.

(30) Foreign Application Priority Data

Sep. 29, 2015 (JP) .............................. JP2015-191727

(51) Int. Cl.
*A61B 5/00* (2006.01)
(52) U.S. Cl.
CPC ............ *A61B 5/0095* (2013.01); *A61B 5/725* (2013.01)
(58) Field of Classification Search
None
See application file for complete search history.

(56) References Cited

U.S. PATENT DOCUMENTS 5,873,830 A * 2/1999 Hossack et al.
2012/0065490 A1 * 3/2012 Zharov et al.
(Continued)

FOREIGN PATENT DOCUMENTS

| CN | 105326524 A | 2/2016 |
|---|---|---|
| CN | 105916446 A | 8/2016 |

(Continued)

OTHER PUBLICATIONS

Chinese Office Action and Search Report for Chinese Application No. 201680052467.8, dated Apr. 14, 2020, with an English translation.

(Continued)

*Primary Examiner* — Katherine L Fernandez
(74) *Attorney, Agent, or Firm* — Birch, Stewart, Kolasch & Birch, LLP

(57) ABSTRACT

A photoacoustic measurement device reducing artifacts caused by photoacoustic waves generated at a surface portion of a subject on which measurement light is incident, and a signal processing method thereof are obtained. A photoacoustic measurement device includes region discrimination unit that discriminates an artifact generation region and an artifact non-generation region in a photoacoustic image on the basis of a positional relationship between a light emitting portion and an acoustic wave detection portion, and filter unit that performs a first filtering process on a first photoacoustic wave detection signal corresponding to a photoacoustic image of the artifact non-generation region and performs a second filtering process on a second photoacoustic wave detection signal corresponding to a photoacoustic image of the artifact generation region. The second filtering process includes further reducing the photoacoustic wave detection signal in a frequency range lower than a prede- (Continued)

termined frequency as compared with the first filtering process.

16 Claims, 10 Drawing Sheets

(56) References Cited

U.S. PATENT DOCUMENTS

| | | | |
|---|---|---|---|
| 2012/0253180 A1* | 10/2012 | Emelianov et al. | |
| 2012/0263180 A1 | 10/2012 | Emelianov et al. | |
| 2012/0296192 A1 | 11/2012 | Fukutani | |
| 2013/0199300 A1 | 8/2013 | Abe | |
| 2013/0245418 A1 | 9/2013 | Oishi | |
| 2013/0245419 A1 | 9/2013 | Oishi | |
| 2013/0261427 A1 | 10/2013 | Oishi | |
| 2013/0276542 A1* | 10/2013 | Herzog et al. | |
| 2014/0018659 A1 | 1/2014 | Fukutani | |
| 2016/0128675 A1* | 5/2016 | Kang et al. | |
| 2016/0212363 A1* | 7/2016 | Kim et al. | |
| 2016/0324423 A1* | 11/2016 | Hashimoto et al. | |
| 2017/0343515 A1 | 11/2017 | Abe | |

FOREIGN PATENT DOCUMENTS

| | | |
|---|---|---|
| JP | 2011-217767 A | 11/2011 |
| JP | 2013-5957 A | 1/2013 |
| JP | 2013-158531 A | 8/2013 |
| JP | 2015-519183 A | 7/2015 |
| KR | 10-2008-0034661 A | 4/2008 |
| WO | WO 2013/188707 A | 12/2013 |
| WO | WO 2014/148375 A1 | 9/2014 |
| WO | WO 2015/048767 A1 | 4/2015 |
| WO | WO 2015/107794 A1 | 7/2015 |
| WO | WO 2015/118881 A1 | 8/2015 |

OTHER PUBLICATIONS

International Preliminary Report on Patentability and Written Opinion of the International Searching Authority (forms PCT/IB/373, PCT/ISA/237 and PCT/IB/326), dated Apr. 12, 2018, for International Application No. PCT/JP2016/004307, with an English translation of the Written Opinion.

International Search Report (form PCT/ISA/210), dated Jan. 24, 2017, for International Application No. PCT/JP2016/004307, with an English translation.

Extended European Search Report, dated Jun. 19, 2018, for European Application No. 16850642.6.

* cited by examiner

PHOTOACOUSTIC MEASUREMENT DEVICE AND SIGNAL PROCESSING METHOD OF PHOTOACOUSTIC MEASUREMENT DEVICE

CROSS-REFERENCE TO RELATED APPLICATION

The present application is a Continuation of PCT International Application No. PCT/JP2016/004307 filed on Sep. 21, 2016, which claims priority under 35 U.S.C. § 119(a) to Japanese Patent Application No. 2015-191727 filed on Sep. 29, 2015. Each of the above applications is hereby expressly incorporated by reference, in its entirety, into the present application.

BACKGROUND

Technical Field

The present invention relates to a photoacoustic measurement device that generates a photoacoustic image on the basis of a photoacoustic signal generated in a subject, and a signal processing method used for the photoacoustic measurement device.

Description of the Related Art

In recent years, a noninvasive measurement method using a photoacoustic effect attracts attention. In this measurement method, pulsed light having a certain appropriate wavelength (for example, a wavelength band of visible light, near-infrared light, or intermediate infrared light) is emitted toward a subject, photoacoustic waves which are elastic waves generated as a result of absorbing substance in the subject absorbing energy of the pulsed light are detected, and a concentration of the absorbing substance is quantitatively measured. The absorbing substance in the subject is, for example, glucose or hemoglobin contained in blood. Further, a technology of detecting such photoacoustic waves and generating a photoacoustic image on the basis of a detection signal is called photoacoustic imaging (PAI) or photoacoustic tomography (PAT).

In photoacoustic imaging, for example, as disclosed in JP2013-158531A and JP2015-519183A, a probe including a light emitting portion that emits measurement light toward a subject, and an acoustic wave detection portion that is provided in parallel to the light emitting portion and detects photoacoustic waves generated in the subject due to the emission of the measurement light is often used.

SUMMARY

The inventors of the present invention have found that in a case where the probe in which the light emitting portion and the acoustic wave detection portion are arranged in parallel as described above is used, photoacoustic waves generated at a surface portion of the subject on which the measurement light is incident propagate on a subject surface, are detected by the acoustic wave detection portion together with other signals, and cause artifacts (a false image). Such artifacts impair diagnostic performance of the displayed photoacoustic image.

JP2013-158531A describes a technology for suppressing artifacts by changing processing for a photoacoustic wave detection signal for each of regions that are different in a depth direction of a subject. Further, JP2015-519183A describes a technology for removing artifacts by performing a low-frequency cutting process on a photoacoustic wave detection signal.

However, the technology described in JP2013-158531A is based on elastography measurement or B mode measurement. With these measurements, an artifact generation region caused by the photoacoustic waves generated at a surface portion of the subject on which the measurement light is incident cannot be detected. Therefore, with the technology described in JP2013-158531A, it is impossible to accurately reduce or remove artifacts caused by photoacoustic waves generated in the surface portion of the subject on which measurement light is incident.

Further, in the technology described in JP2015-519183A, the low-frequency cutting process is performed without recognition of a region in which artifacts are generated. Therefore, with this technology, it is impossible to accurately reduce or remove the artifacts caused by the photoacoustic waves generated at the surface portion of the subject on which the measurement light is incident.

The present invention has been made in view of the above problems, and an object of the present invention is to provide a photoacoustic measurement device capable of accurately reducing or removing artifacts caused by photoacoustic waves generated at a surface portion of a subject on which measurement light is incident, and a signal processing method that is used in the photoacoustic measurement device.

A photoacoustic measurement device according to the present invention comprises: a probe including a light emitting portion that emits measurement light to a subject, and an acoustic wave detection portion that is arranged in parallel to the light emitting portion and detects photoacoustic waves generated in the subject due to emission of the measurement light; an image generation unit that generates a photoacoustic image on the basis of a photoacoustic wave detection signal output by the acoustic wave detection portion; a region discrimination unit that discriminates an artifact generation region and an artifact non-generation region in the photoacoustic image on the basis of at least a positional relationship between the light emitting portion and the acoustic wave detection portion; and a filter unit that performs a first filtering process on a first photoacoustic wave detection signal corresponding to a photoacoustic image of the artifact non-generation region discriminated by the region discrimination unit among the photoacoustic wave detection signals, and performing a second filtering process on a second photoacoustic wave detection signal corresponding to a photoacoustic image of the artifact generation region discriminated by the region discrimination unit among the photoacoustic wave detection signals, wherein the second filtering process includes further reducing the photoacoustic wave detection signal in a frequency range lower than a predetermined frequency as compared with the first filtering process.

The "photoacoustic wave detection signal", the "first photoacoustic wave detection signal", and the "second photoacoustic wave detection signal" include not only a signal output from an acoustic wave detection unit that detects photoacoustic waves, but also a signal (including digitized data) after such a signal is subjected to any processing.

Further, the "predetermined frequency" does not mean a certain frequency with a certain value, but means a predetermined frequency. A value thereof can be arbitrarily set.

In the photoacoustic measurement device of the present invention, it is preferable that the filter unit includes a band pass filter that performs a band pass filtering process, and the band pass filtering process as the second filtering process includes setting a cutoff frequency on the low frequency side to be on the higher frequency side as compared with the band pass filtering process as the first filtering process.

Further, in the photoacoustic measurement device of the present invention, the filter unit may include a high pass filter that performs a high pass filtering process, and the high pass filtering process as the second filtering process may include setting a cutoff frequency to be on a higher frequency side as compared with the high pass filtering process as the first filtering process.

Further, in the photoacoustic measurement device of the present invention, it is preferable that the region discrimination unit discriminates the artifact generation region and the artifact non-generation region on the basis of a correspondence table in which a positional relationship between the light emitting portion and the acoustic wave detection portion is associated with a boundary between the artifact generation region and the artifact non-generation region.

Further, in the photoacoustic measurement device of the present invention, the region discrimination unit may discriminate the artifact generation region and the artifact non-generation region using a calculation equation for calculating a boundary between the artifact generation region and the artifact non-generation region from a positional relationship between the light emitting portion and the acoustic wave detection portion.

Further, in the photoacoustic measurement device of the present invention, it is preferable that the region discrimination unit corrects the discrimination according to a sound speed at a portion of a subject through which the photoacoustic waves propagate.

Further, in the photoacoustic measurement device of the present invention, it is preferable that the filter unit performs a boundary region filtering process different from the first filtering process and the second filtering process on a photoacoustic wave detection signal corresponding to a photoacoustic image of at least one boundary region set in a range including the boundary between the artifact non-generation region and the artifact generation region.

It is preferable that the boundary region filtering process is an intermediate filtering process between the first filtering process and the second filtering process.

Further, it is preferable that pass characteristics of the boundary region filtering process are determined according to a subject depth direction position of the boundary region on the basis of pass characteristics of the first filtering process and pass characteristics of the second filtering process.

Further, in the photoacoustic measurement device of the present invention, it is preferable that an image corresponding to a photoacoustic image of at least one boundary region set in a range including a boundary between the artifact non-generation region and the artifact generation region is formed using a signal obtained by performing weighted adding on the first photoacoustic wave detection signal subjected to the first filtering process and the second photoacoustic wave detection signal subjected to the second filtering process according to a subject depth direction position of the boundary region.

Meanwhile, a signal processing method of a photoacoustic measurement device according to the present invention is the signal processing method of the photoacoustic measurement device comprising a probe including a light emitting portion that emits measurement light to a subject, and an acoustic wave detection portion that is arranged in parallel to the light emitting portion and detects photoacoustic waves generated in the subject due to emission of the measurement light, and an image generation unit that generates a photoacoustic image on the basis of a photoacoustic wave detection signal output by the acoustic wave detection portion, the signal processing method comprising: discriminating an artifact generation region and an artifact non-generation region in the photoacoustic image on the basis of at least a positional relationship between the light emitting portion and the acoustic wave detection portion; performing a first filtering process on a first photoacoustic wave detection signal corresponding to a photoacoustic image of the artifact non-generation region among the photoacoustic wave detection signals; performing a second filtering process on a second photoacoustic wave detection signal corresponding to a photoacoustic image of the artifact generation region among the photoacoustic wave detection signals; and further reducing the photoacoustic wave detection signal in a frequency range lower than a predetermined frequency in the second filtering process as compared with the first filtering process.

In the signal processing method of a photoacoustic measurement device according to the present invention, it is preferable that the filtering process is a band pass filtering process, and the band pass filtering process as the second filtering process includes setting a cutoff frequency on the low frequency side to be on a higher frequency side as compared with the band pass filtering process as the first filtering process.

Further, in the signal processing method of a photoacoustic measurement device according to the present invention, the filtering process may be a high pass filtering process, and the high pass filtering process as the second filtering process may include setting a cutoff frequency to be on a higher frequency side as compared with the high pass filtering process as the first filtering process.

Further, in the signal processing method of a photoacoustic measurement device according to the present invention, it is preferable that the artifact generation region and the artifact non-generation region are discriminated on the basis of a correspondence table in which a positional relationship between the light emitting portion and the acoustic wave detection portion is associated with a boundary between the artifact generation region and the artifact non-generation region.

Alternatively, in the signal processing method of a photoacoustic measurement device according to the present invention, the artifact generation region and the artifact non-generation region may be discriminated using a calculation equation for calculating a boundary between the artifact generation region and the artifact non-generation region from a positional relationship between the light emitting portion and the acoustic wave detection portion.

Further, in the signal processing method of a photoacoustic measurement device according to the present invention, it is preferable that the discrimination is corrected according to a sound speed at a portion of a subject through which the photoacoustic waves propagate.

Further, in the signal processing method of a photoacoustic measurement device according to the present invention, it is preferable that a boundary region filtering process different from the first filtering process and the second filtering process is performed on a photoacoustic wave detection signal corresponding to a photoacoustic image of at least one boundary region set in a range including the boundary between the artifact non-generation region and the artifact generation region.

It is preferable that the boundary region filtering process is an intermediate filtering process between the first filtering process and the second filtering process.

It is preferable that pass characteristics of the boundary region filtering process is determined according to a subject depth direction position of the boundary region on the basis of pass characteristics of the first filtering process and pass characteristics of the second filtering process.

Further, it is preferable that the signal processing method of a photoacoustic measurement device according to the present invention further comprises forming an image corresponding to a photoacoustic image of at least one boundary region set in a range including a boundary between the artifact non-generation region and the artifact generation region using a signal obtained by performing weighted adding on the first photoacoustic wave detection signal subjected to the first filtering process and the second photoacoustic wave detection signal subjected to the second filtering process according to a subject depth direction position of the boundary region.

Since the photoacoustic measurement device according to the present invention includes a probe including a light emitting portion that emits measurement light to a subject, and an acoustic wave detection portion that is arranged in parallel to the light emitting portion and detects photoacoustic waves generated in the subject due to emission of the measurement light; an image generation unit that generates a photoacoustic image on the basis of a photoacoustic wave detection signal output by the acoustic wave detection portion; a region discrimination unit for discriminating an artifact generation region and an artifact non-generation region in the photoacoustic image on the basis of at least a positional relationship between the light emitting portion and the acoustic wave detection portion; and a filter unit for performing a first filtering process on a first photoacoustic wave detection signal corresponding to a photoacoustic image of the artifact non-generation region discriminated by the region discrimination unit among the photoacoustic wave detection signals, and performs a second filtering process on a second photoacoustic wave detection signal corresponding to a photoacoustic image of the artifact generation region discriminated by the region discrimination unit among the photoacoustic wave detection signals, and the second filtering process includes further reducing the photoacoustic wave detection signal in a frequency range lower than a predetermined frequency as compared with the first filtering process, it is possible to accurately reduce or remove artifacts caused by the photoacoustic waves generated at the surface portion of the subject on which the measurement light is incident.

BRIEF DESCRIPTION OF THE DRAWINGS

Exemplary embodiments of the present invention will be described in detail based on the following figures, wherein.

DETAILED DESCRIPTION

Hereinafter, embodiments of the present invention will be described in detail with reference to the drawings.

Figure 1:
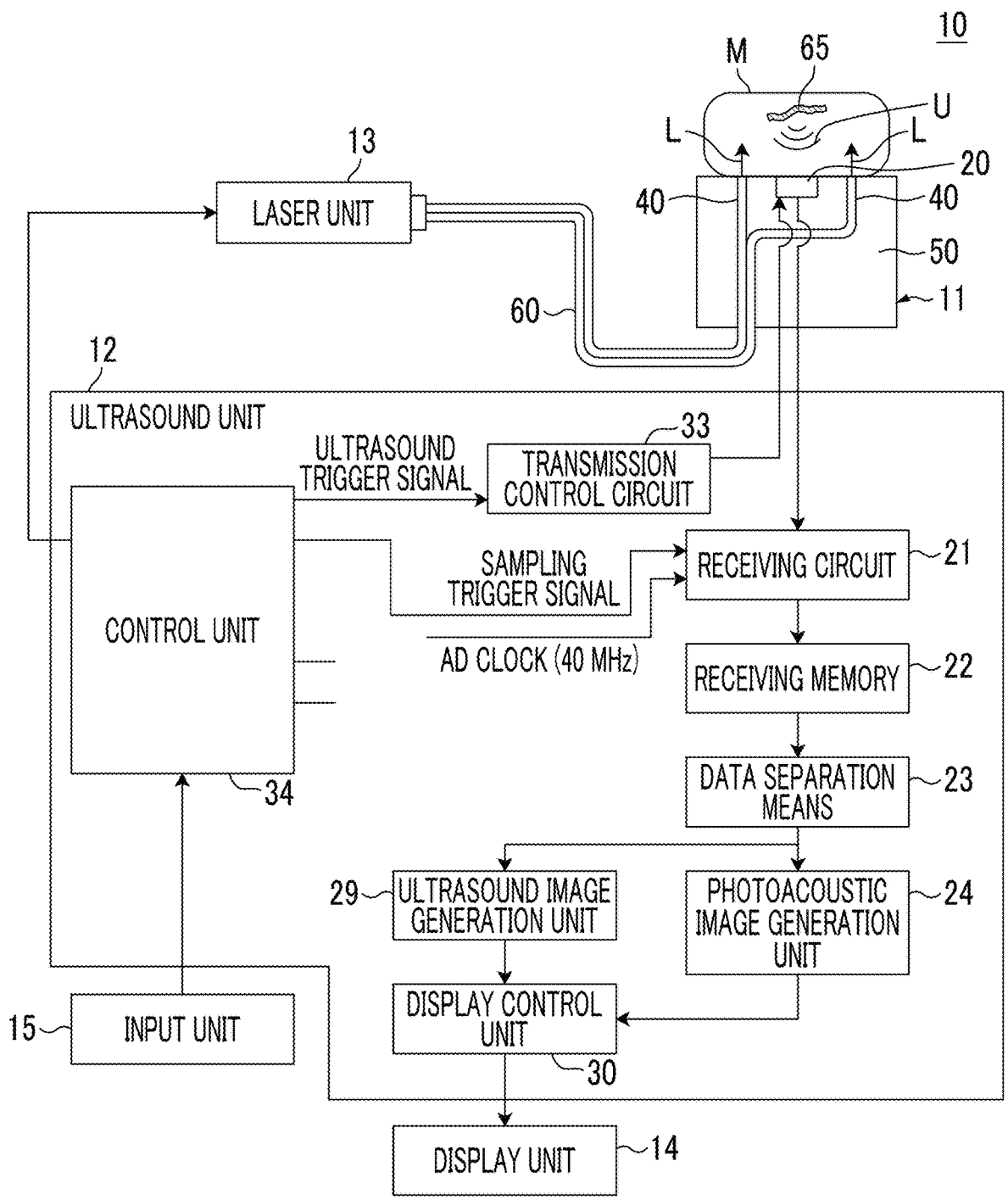
FIG. 1 is a schematic diagram illustrating an overall configuration of a photoacoustic measurement device according to an embodiment of the present invention.

FIG. 1 is a schematic diagram illustrating an overall configuration of a photoacoustic measurement device 10 according to an embodiment of the present invention. In FIG. 1, a shape of the probe 11 is schematically shown. The photoacoustic measurement device 10 of the embodiment has, for example, a function of generating a photoacoustic image on the basis of a photoacoustic signal. As schematically illustrated in FIG. 1, the photoacoustic measurement device 10 includes a probe 11 configured as an ultrasonic probe, an ultrasonic unit 12, a laser unit 13, a display unit 14, an input unit 15, and the like. These components will be sequentially described below.

The probe 11 has, for example, a function of emitting measurement light and ultrasonic waves toward a subject M that is a living body, and a function of detecting acoustic waves U propagating in the subject M. That is, the probe 11 can perform emission (transmission) of ultrasonic waves to the subject M, and detection (reception) of reflected ultrasonic waves (reflected acoustic waves) reflected at and returned from the subject M.

The "acoustic waves" as used herein are a term including ultrasonic waves and photoacoustic waves. Here, the "ultrasonic waves" means elastic waves transmitted by a probe and reflected waves thereof, and the "photoacoustic waves" means elastic waves emitted by the absorber 65 absorbing the measurement light. Further, the acoustic waves emitted from the probe 11 are not limited to the ultrasonic waves, and acoustic waves at an audible frequency may be used as long as an appropriate frequency is selected according to a subject, measurement conditions, or the like. The absorber 65 in the subject M may be, for example, a blood vessel, a metal member, or the like.

Generally, for the probe 11, a probe corresponding to sector scanning, a probe corresponding to linear scanning, and a probe corresponding to convex scanning, and the like is prepared, and an appropriate probe is selected from among the probes according to an imaging part and is used. Further, an optical fiber 60 serving as a connection unit that guides laser light L which is measurement light emitted from the laser unit 13 described below to a light emitting portion 40 is connected to the probe 11.

The probe 11 includes a vibrator array 20 which is an acoustic wave detector, a total of two light emitting portions 40 arranged one by one on both sides of the vibrator array 20 with the vibrator array 20 interposed therebetween, and a casing 50 in which, for example, the vibrator array 20 and the two light emitting portions 40 are accommodated.

In the embodiment, the vibrator array 20 also functions as an ultrasonic wave transmission element. The vibrator array 20 is connected to, for example, a circuit for ultrasonic wave transmission, a circuit for acoustic wave reception via a wire (not illustrated).

The vibrator array 20 includes a plurality of ultrasonic vibrators which are electroacoustic transducer elements arranged side by side in one direction. The ultrasonic vibrator is, for example, piezoelectric ceramics or a piezoelectric element configured of a polymer film such as polyvinylidene fluoride (PVDF). The ultrasonic vibrator has a function of converting the received acoustic wave U into an electric signal. The vibrator array 20 may include an acoustic lens.

As described above, the vibrator array 20 in the embodiment is a vibrator array in which a plurality of ultrasonic vibrators are one-dimensionally arranged, but a vibrator array in which a plurality of ultrasonic vibrators are two-dimensionally arranged may be used.

The ultrasonic vibrator also has a function of transmitting ultrasonic waves, as described above. That is, in a case where an alternating voltage is applied to the ultrasonic vibrator, the ultrasonic vibrator generates ultrasonic waves at a frequency corresponding to a frequency of the alternating voltage. Transmission and reception of ultrasonic waves may be separated from each other. That is, for example, transmission of the ultrasonic waves may be performed from a position different from the probe 11, and reflected ultrasonic waves with respect to the transmitted ultrasonic waves may be received by the probe 11.

The light emitting portion 40 is a portion that emits the laser light L guided by the optical fiber 60 toward the subject M. In the embodiment, the light emitting portion 40 is configured by a distal end portion of the optical fiber 60, that is, an end portion far from the laser unit 13 which is a light source for the measurement light. As illustrated in FIG. 1, in this embodiment, two light emitting portions 40 are arranged on both sides, for example, in an elevation direction of the vibrator array 20 with the vibrator array 20 interposed therebetween. In a case where a plurality of ultrasonic vibrators are one-dimensionally arranged, the elevation direction is a direction perpendicular to an arrangement direction of the vibrators and parallel to a detection surface of the vibrator array 20.

The light emitting portion may include a light guide plate and a diffusion plate optically coupled to a distal end of the optical fiber 60. Such a light guide plate can be configured by, for example, an acrylic plate or a quartz plate. Further, a lens diffusion plate in which microlenses are randomly arranged on a substrate, a quartz plate in which, for example, diffusing fine particles are dispersed, or the like may be used as the diffusion plate. A holographic diffusion plate or an engineering diffusion plate may be used as the lens diffusion plate.

The laser unit 13 illustrated in FIG. 1 includes, for example, a flash lamp excitation Q-switched solid state laser, such as a Q-switched alexandrite laser, and emits laser light L as measurement light. The laser unit 13 is configured to receive a trigger signal from the control unit 34 of the ultrasonic unit 12 and output the laser light L. It is preferable that the laser unit 13 outputs pulsed laser light L having a pulse width of 1 to 100 nsec (nanoseconds).

A wavelength of the laser light L is appropriately selected according to light absorption characteristics of the absorber 65 in the subject M that is a measurement target. For example, in a case where the measurement target is hemoglobin in the living body, that is, in a case where blood vessels are imaged, it is generally preferable that the wavelength is a wavelength belonging to a near infrared wavelength range. The near infrared wavelength range means a wavelength range of about 700 to 850 nm. However, the wavelength of the laser light L is naturally not limited to this. Further, the laser light L may be laser light having a single wavelength or may be laser light including a plurality of wavelengths such as 750 nm and 800 nm, for example. In the case where the laser light L includes the plurality of wavelengths, light including the wavelengths may be emitted at the same time, or may be emitted while being alternatively switched.

The laser unit 13 may be configured using a second harmonic generation (YAG-SHG)-optical parametric oscillation (OPO) laser capable of similarly outputting laser light in a near infrared wavelength range, or a titanium-sapphire (Ti-Sapphire) laser, or the like, in addition to the above-described alexandrite laser.

The optical fiber 60 guides the laser light L emitted from the laser unit 13 to the two light emitting portions 40. The optical fiber 60 is not particularly limited, and a known optical fiber such as a quartz fiber can be used. For example, one thick optical fiber may be used, or a bundle fiber in which a plurality of optical fibers are bundled may be used. For example, in a case where the bundle fiber is used, the bundle fiber is arranged so that the laser light L is incident from a light incidence end face of one integrated fiber portion, and a distal portion of each of fiber portions branched in two in the bundle fiber constitutes the light emitting portion 40 as described above.

The ultrasonic unit 12 includes a reception circuit 21, a reception memory 22, data separation means 23, a photoacoustic image generation unit 24, an ultrasonic image generation unit 29, a display control unit 30, a transmission control circuit 33, and a control unit 34.

The control unit 34 controls each unit of the photoacoustic measurement device 10, and includes a trigger control circuit (not illustrated) in this embodiment. For example, in a case where a photoacoustic image is acquired, the trigger control circuit sends an optical trigger signal to the laser unit 13. Accordingly, a flash lamp that is an excitation source is lit in the Q-switched solid state laser of the laser unit 13, and excitation of a laser rod is started. While an excitation state of the laser rod is being maintained, the laser unit 13 enters a state in which the laser unit 13 can output the laser light L.

The control unit 34 then transmits a Q switch trigger signal from the trigger control circuit to the laser unit 13.

That is, the control unit 34 controls an output timing of the laser light L from the laser unit 13 using this Q switch trigger signal. The control unit 34 transmits a sampling trigger signal to the reception circuit 21 simultaneously with the transmission of the Q switch trigger signal. This sampling trigger signal specifies a sampling start timing of the photoacoustic signal in an analog to digital converter (AD converter) of the reception circuit 21. Thus, by using the sampling trigger signal, the photoacoustic signal can be sampled in synchronization with the output of the laser light L.

In a case where an ultrasonic image is acquired, the control unit 34 transmits an ultrasonic transmission trigger signal to instruct the transmission control circuit 33 to transmit ultrasonic waves. In a case where the transmission control circuit 33 receives the ultrasonic transmission trigger signal, the transmission control circuit 33 causes the probe 11 to transmit the ultrasonic waves. The control unit 34 transmits a sampling trigger signal to the reception circuit 21 at a timing of the ultrasonic transmission to start sampling of a reflected ultrasonic signal.

In a case where the photoacoustic image or the ultrasonic image described above is acquired, the probe 11 is slightly shifted in position, for example, in the above-described elevation direction with respect to the subject M, and the subject M is scanned by the laser light L or ultrasonic waves. Therefore, sampling of the photoacoustic signal or the reflected ultrasonic signal is performed while shifting acoustic wave detection lines line by line, in synchronization with the scanning. The scanning may be performed by an operator manually moving the probe 11, or may be performed using an automatic scanning mechanism.

The reception circuit 21 receives the photoacoustic wave detection signal output by the vibrator array 20 of the probe 11 and stores the received detection signal in the reception memory 22. The reception circuit 21 typically includes a low noise amplifier, a variable gain amplifier, a low pass filter, and an AD converter. The photoacoustic wave detection signal output by the probe 11 is amplified by the low noise amplifier, gain adjustment is performed according to the depth in the variable gain amplifier, a high frequency component is cut by the low pass filter, and then, the signal is converted into a digital signal in the AD converter and stored in the reception memory 22. The reception circuit 21 is configured by, for example, one integrated circuit (IC). The cut of the high frequency component in the low pass filter is intended to prevent aliasing noise from being generated at the time of AD conversion. In general, a cutoff frequency is about 10 MHz to 30 MHz, which is about a half of the sampling frequency of the AD conversion.

In the embodiment, the probe 11 outputs the photoacoustic wave detection signal and a reflected ultrasonic detection signal. Therefore, the reception memory 22 stores a photoacoustic wave detection signal and a reflected ultrasonic detection signal which have been digitized. The data separation means 23 reads the data for a photoacoustic image, that is, the digitized photoacoustic wave detection signal from the reception memory 22, and transmits the digitized photoacoustic wave detection signal to the photoacoustic image generation unit 24. Further, the data separation means 23 reads the data for a reflected ultrasonic image, that is, the digitized reflected ultrasonic detection signal from the reception memory 22, and transmits the digitized reflected ultrasonic detection signal to the ultrasonic image generation unit 29.

The photoacoustic image generation unit 24 reconstructs the photoacoustic wave detection signal received from the reception memory 22 to generate a photoacoustic image. Specifically, the photoacoustic image generation unit 24 adds the photoacoustic wave detection signal based on the signal from each ultrasonic vibrator with a delay time according to a position of each ultrasonic vibrator of the vibrator array 20, to generate a photoacoustic wave detection signal for one line (delayed addition method). The photoacoustic image generation unit 24 may perform the reconstruction using a circular back projection (CBP) method instead of the delayed addition method. Alternatively, the photoacoustic image generation unit 24 may perform the reconstruction using a Hough transform method or a Fourier transform method. The reconstructed photoacoustic wave detection signals for a plurality of lines are sent to the display control unit 30 as a signal for displaying the photoacoustic image (tomographic image) through signal processing such as a detection process and a logarithmic conversion process.

The photoacoustic wave detection signals for a plurality of lines have been subjected to processing such as digitization or reconstruction and are not the photoacoustic wave detection signals themselves output by the vibrator array 20 of the probe 11. However, since the photoacoustic wave detection signals are signals based on the photoacoustic wave detection signal output by the vibrator array 20, the photoacoustic wave detection signals are referred to as "photoacoustic wave detection signals". Further, in the embodiment, the photoacoustic image generation unit 24 performs the above-described filtering process, which will be described in detail below.

The ultrasonic image generation unit 29 basically performs the same process as that for the photoacoustic wave detection signal on the reflected ultrasonic detection signal stored in the reception memory 22 to generate a reflected ultrasonic detection signal for a plurality of lines indicating the ultrasonic image (tomographic image). The ultrasonic image generation unit 29 outputs the thus generated reflected ultrasonic detection signal to the display control unit 30.

The display control unit 30 causes the display unit 14 to display the photoacoustic image on the basis of the photoacoustic wave detection signal and an ultrasonic image on the basis of the reflected ultrasonic detection signal. The two images are separately displayed on the display unit 14 or are combined and displayed on the display unit 14 as a combined image. In the latter case, the display control unit 30, for example, superimposes the photoacoustic image and the ultrasonic image and performs image combination. Thus, in a case where the ultrasonic image is generated and displayed in addition to the photoacoustic image, a portion which cannot be formed as an image in the photoacoustic image can be observed in the ultrasonic image.

Next, preventing the above-described artifact from being generated in the photoacoustic measurement device 10 having the basic configuration as described above will be described. First, this artifact will be described in detail with reference to FIGS. 2 and 3A-3F.

Figure 2:
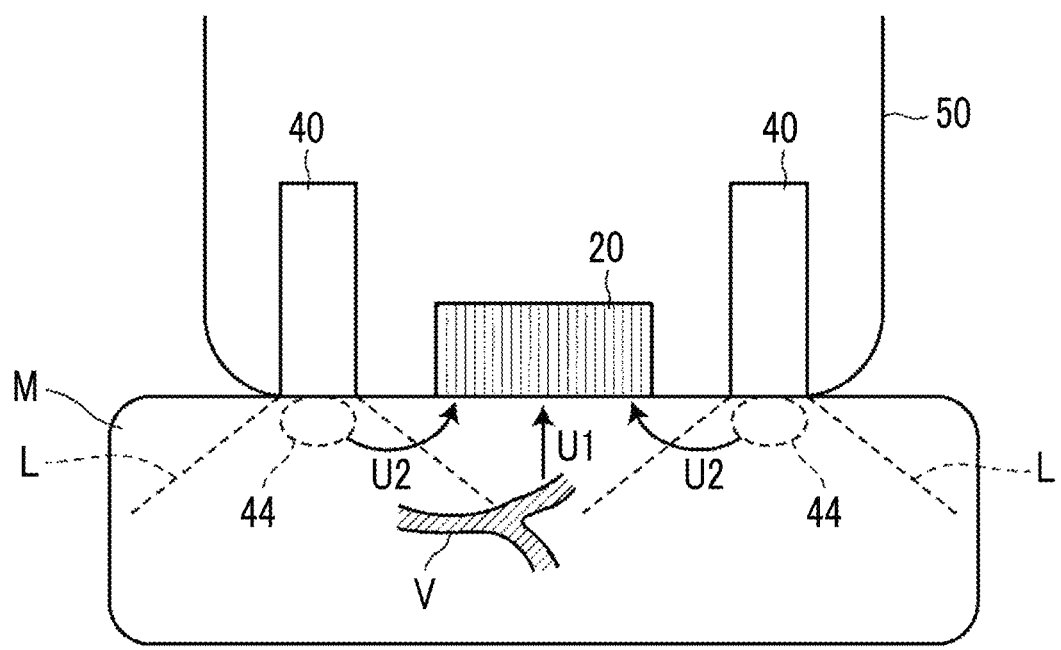
FIG. 2 is a diagram illustrating generation of a false image.

FIG. 2 is a schematic diagram illustrating a state in which photoacoustic waves generated from a blood vessel V that is an example of the absorber 65 illustrated in FIG. 1 and photoacoustic waves generated on a surface of the subject on which the measurement light is incident are detected. Ideally, it is preferable to detect only photoacoustic waves U1 from the blood vessel V in a case where the subject M is irradiated with the measurement light L. However, actually, photoacoustic waves U2 generated at a subject surface portion 44 on which the measurement light L is incident is also detected. This photoacoustic waves U2 cause artifacts (a false image). A time from generation of the photoacoustic waves U2 to detection thereof depends on a distance between the light emitting portion 40 and the vibrator array 20 (or an individual ultrasonic vibrator; the same applies hereinafter) and, more specifically, a distance between an arrival region on an abutment plane of the measurement light L and the acoustic wave detection portion. That is, as the distance between the light emitting portion 40 and the vibrator array 20 increases, a distance by which the photoacoustic waves U2 travels through the subject increases, and therefore, the time from the generation of the photoacoustic waves U2 to the detection thereof increases.

The "abutment plane" means a plane that passes through a distal end of the probe 11 (that is, an intersection between a probe surface in contact with the subject M and a central axis of the acoustic wave detection portion) and is parallel to a detection surface of the acoustic wave detection portion. Further, the "arrival region" means a region in which the abutment plane and the measurement light L intersect each other.

Figure 3A:
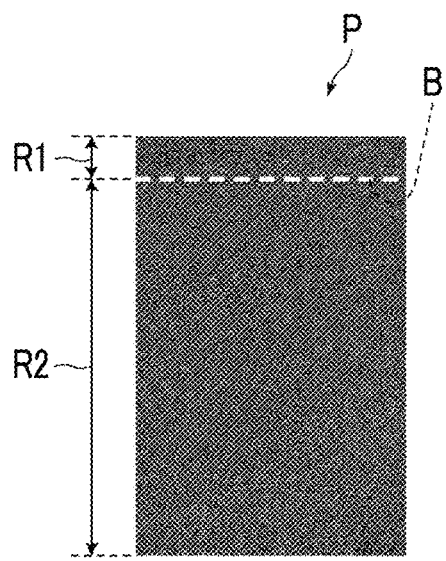
FIG. 3A is a diagram illustrating photoacoustic images in which an artifact region is generated due to photoacoustic waves generated on a subject surface.
Figure 3B:
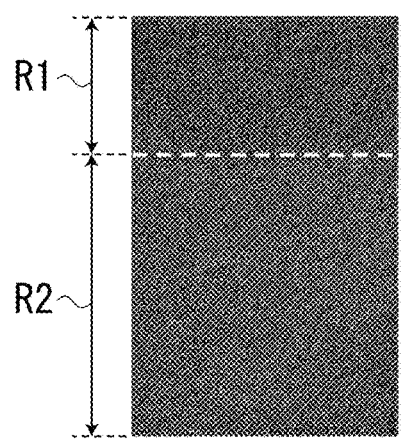
FIG. 3B is a diagram illustrating photoacoustic images in which an artifact region is generated due to photoacoustic waves generated on a subject surface.
Figure 3C:
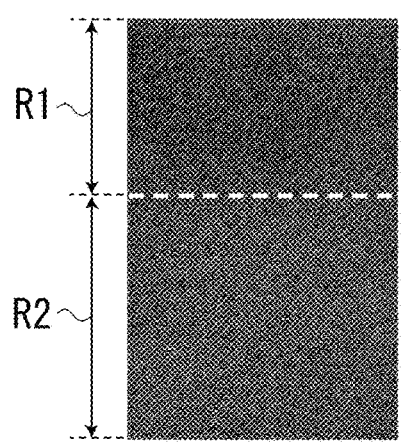
FIG. 3C is a diagram illustrating photoacoustic images in which an artifact region is generated due to photoacoustic waves generated on a subject surface.
Figure 3D:
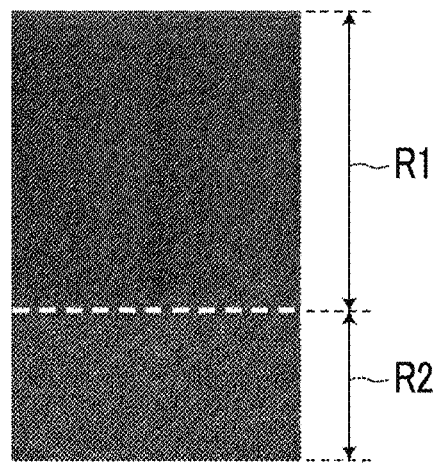
FIG. 3D is a diagram illustrating photoacoustic images in which an artifact region is generated due to photoacoustic waves generated on a subject surface.
Figure 3E:
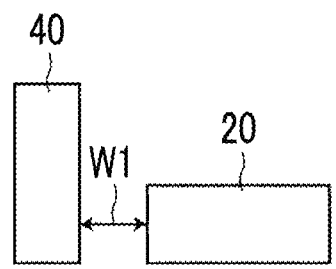
FIG. 3E is a schematic diagram illustrating a positional relationship between a light emitting portion and a vibrator array in a case where the photoacoustic image of FIG. 3A is generated.
Figure 3F:
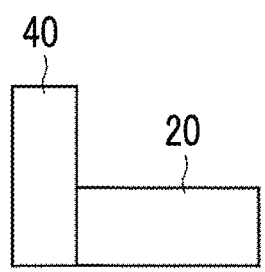
FIG. 3F is a schematic diagram illustrating a positional relationship between a light emitting portion and a vibrator array in a case where the photoacoustic image of FIG. 3D 3 is generated.

A time from generation of the photoacoustic waves U2 to detection thereof affects the range in which the artifact region appears in the photoacoustic image. FIG. 3A to FIG. 3F illustrates states in which sizes of an observation region (artifact non-generation region) R1 and the artifact generation region R2 changes depending on a distance W1 between the light emitting portion 40 and the vibrator array 20. Specifically, FIG. 3A to FIG. 3D are diagrams illustrating photoacoustic images P in which the artifact generation region R2 is generated due to the photoacoustic waves U2 generated on the surface of the subject. Further, FIG. 3E and FIG. 3F are schematic diagrams illustrating a positional relationship between the light emitting portion 40 and the vibrator array 20 in a case where the photoacoustic images P of FIG. 3A and FIG. 3D are generated, respectively.

Figure 4:
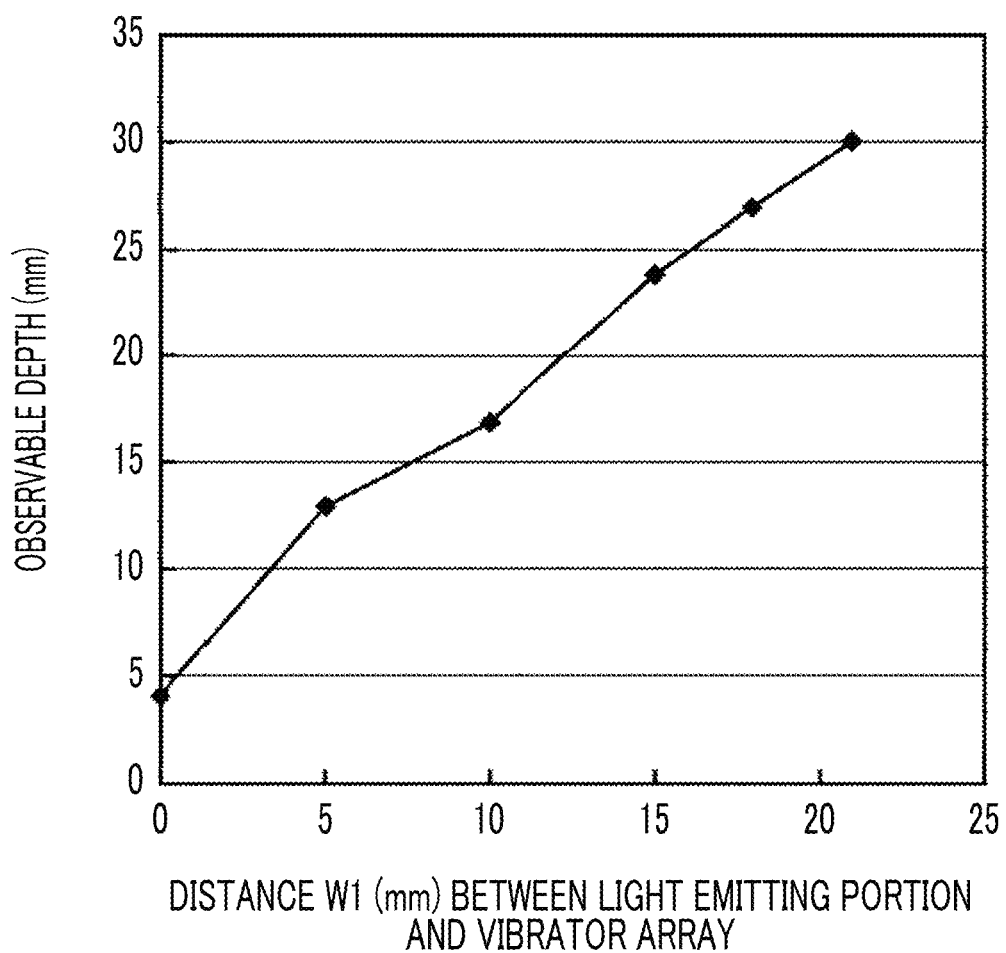
FIG. 4 is a graph illustrating an example of a relationship between a distance between the light emitting portion and the vibrator array, and an observable depth.

It can be seen from FIG. 3A to FIG. 3F that a boundary B between the artifact non-generation region R1 and the artifact generation region R2 is lowered as the distance W1 between the light emitting portion 40 and the vibrator array 20 increases, that is, the boundary B moves to a deeper side of the subject M. This is because a vertical direction of the photoacoustic image P corresponds to a time axis, and a time until the signal of the photoacoustic waves U2 is detected is delayed as the distance W1 between the light emitting portion 40 and the vibrator array 20 increases. FIG. 4 illustrates an example of a relationship between the boundary B between the artifact non-generation region R1 and the artifact generation region R2 with respect to a distance W1 between the light emitting portion 40 and the vibrator array 20 described above. A horizontal axis in FIG. 4 is the above-described distance W1, and an "observable depth" on a vertical axis is a depth of the artifact non-generation region R1, that is, a depth position of the boundary B.

On the basis of the above findings, in the embodiment, as an example, the following filtering process is performed by a band pass filter in the photoacoustic image generation unit 24 of FIG. 1. This filtering process is performed by arithmetic processing on the basis of a previously given program.

This band pass filtering process is performed on the photoacoustic wave detection signal (first photoacoustic wave detection signal) corresponding to a photoacoustic image of the artifact non-generation region R1 and the photoacoustic wave detection signal (second photoacoustic wave detection signal) corresponding to a photoacoustic image of the artifact generation region R2 among the photoacoustic wave detection signals reconstructed as described above and representing photoacoustic images while changing pass characteristics of the filter. Here, the band pass filtering process for the first photoacoustic wave detection signal is referred to as a first band pass filtering process (a first filtering process in the present invention), and the second band pass filtering process for the second photoacoustic wave detection signal is referred to as a second band pass filtering process (a second filtering process in the present invention).

Figure 5:
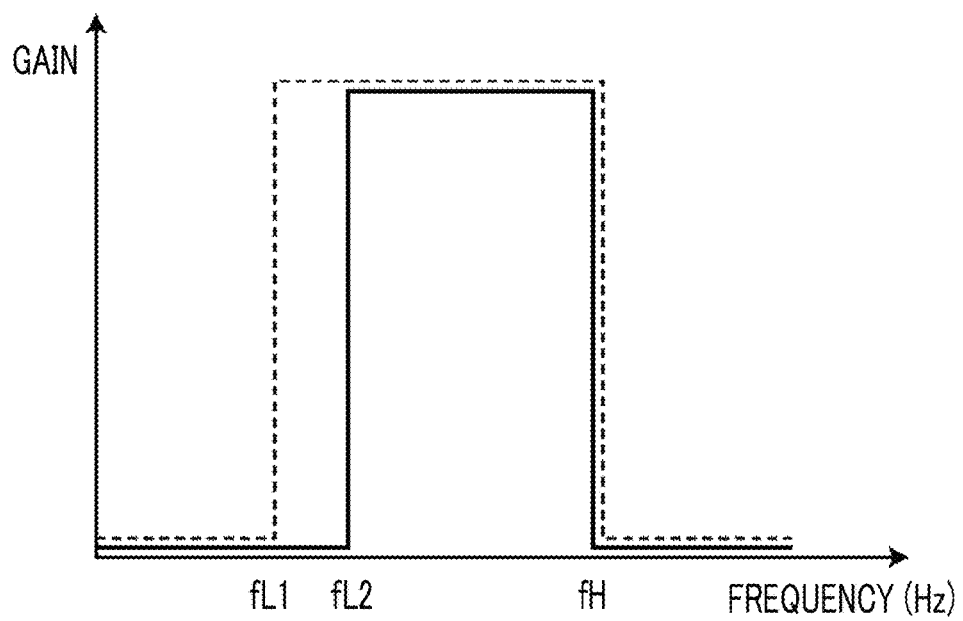
FIG. 5 is a schematic diagram illustrating an example of pass characteristics of a filter.

FIG. 5 illustrates basic pass characteristics of the band pass filtering process. In FIG. 5, a broken line indicates the pass characteristics in the first band pass filtering process, and a solid line indicates the pass characteristics in the second band pass filtering process. That is, a cutoff frequency $fL2$ on the low frequency side for the second photoacoustic wave detection signal is set to be on a higher frequency side than a cutoff frequency $fL1$ on the low frequency side for the first photoacoustic wave detection signal. More specifically, for example, in a case where a detection center frequency of the vibrator array 20 of the probe 11 is 6.5 MHz, the cutoff frequency $fL1$ on the low frequency side for the first photoacoustic wave detection signal is about 1 MHz, the cutoff frequency $fH$ on the high frequency side for the first photoacoustic wave detection signal is about 10 MHz, the cutoff frequency $fL2$ on the low frequency side for the second photoacoustic wave detection signal is about 2 MHz, and the cutoff frequency $fH$ on the high frequency side for the second photoacoustic wave detection signal is about 10 MHz.

As described above, in the embodiment, the second band pass filtering process for the second photoacoustic wave detection signal includes further reducing the photoacoustic wave detection signal in a frequency range lower than a predetermined frequency (2 MHz) as compared with the first band pass filtering process for the first photoacoustic wave detection signal. Here, the "frequency range lower than a predetermined frequency" is not limited to the frequency range lower than 2 MHz, but may be a frequency range having a certain width existing on the lowest frequency side of the photoacoustic wave detection signal, and a numerical value of the "predetermined frequency" may be appropriately set.

As described above with reference to FIG. 2, since the photoacoustic waves U2 generated in the subject surface portion 44 and causing artifacts are generated from the entire surface portion of the subject M on which the laser light L is incident, a signal obtained by detecting the photoacoustic waves U2 becomes a signal in a relatively low frequency range. Therefore, as described above, in a case where more signal components in the low frequency range of the second photoacoustic wave detection signal are removed as compared with the first photoacoustic wave detection signal, the artifacts are no longer generated or are reduced in the artifact generation region R2 of the photoacoustic image displayed on the display unit 14. On the other hand, in the artifact non-generation region R1, diagnostically significant signal components in a low frequency range of the subject M are not inadvertently removed. Therefore, in the display unit 14, a photoacoustic image with high diagnostic performance as a whole can be displayed. On the other hand, in the technology described in JP2015-519183A described above, diagnostically significant signal components in the low frequency range are likely to be removed.

It is necessary to know the boundary B between the artifact non-generation region R1 and the artifact generation region R2 in order to discriminate the artifact non-generation region R1 and the artifact generation region R2. As described above with reference to FIGS. 3A-3F and 4, the subject depth direction position of the boundary B basically corresponds to the distance W1 between the light emitting portion 40 and the vibrator array 20. Therefore, in the embodiment, a correspondence table between the subject depth direction position of the boundary B for each probe 11 and the distance W1 is stored in the form of a lookup table in an internal memory of the photoacoustic image generation unit 24 illustrated in FIG. 1, and the photoacoustic image generation unit 24 discriminates the boundary B, that is, the artifact non-generation region R1 and the artifact generation region R2 by referring to this lookup table. By doing so, even in a case where a plurality of types of probes 11 are interchangeably attached to the photoacoustic measurement device 10, recognition information of the probe 11 to be used is received from, for example, the input unit 15, and the artifact non-generation region R1 and the artifact generation region R2 can be correctly discriminated for the probe 11. As is obvious from the above description, in the embodiment, the photoacoustic image generation unit 24 constitutes region discrimination unit and filter unit in the present invention.

Here, as the filter unit, it is preferable to use filter unit in which influence of side lobes is reduced by a window function such as a Hamming window, a Hanning window, a Blackman window, or a Kaiser window.

A relationship between the subject depth direction position of the boundary B and the distance W1 changes according to sound velocity at an observation part, that is, sound speed at a part of the subject M in which the photoacoustic waves propagate. Therefore, the relationship between the subject depth direction position of the boundary B and the distance W1 in the correspondence table may be corrected according to the sound speed. Through this correction, the subject depth direction position of the boundary B is corrected, that is, the discrimination between the artifact non-generation region R1 and the artifact generation region R2 is corrected.

The sound velocity may be input from the input unit 15 illustrated in FIG. 1, or a correspondence relationship between the sound velocity and the observation part may be stored in a storage unit (not illustrated), and the sound speed may be recognized by referring to the correspondence relationship from the information on the observation part input from the input unit 15.

Further, the relationship may be corrected on the basis of at least one of intensity of the laser L that is the measurement light, a pulse width of the laser L, or the presence or absence of an acoustic member on a detection surface of the vibrator array 20, in addition to correcting the relationship between the subject depth direction position of the boundary B and the distance W1 according to the sound speed.

Further, a calculation equation for calculating the subject depth direction position of the boundary B from the distance W1 may be stored, and the boundary B may be obtained from the distance W1 input from the input unit 15 shown in FIG. 1 using the above calculation equation, instead of obtaining the boundary B from the correspondence table between the subject depth direction position of the boundary B and the distance W1.

Further, the operator may input information for designating the boundary B from the input unit 15 while confirming the display of the artifact non-generation region R1 and the artifact generation region R2 shown on the display unit 14.

Figure 11:
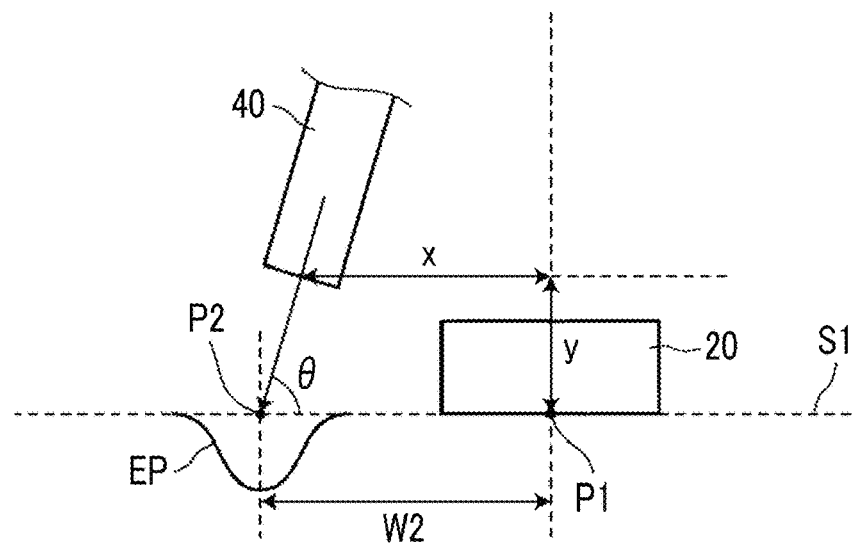
FIG. 11 is a diagram illustrating a distance between a light emitting portion and a vibrator array.

The information for designating the boundary B may not be information indicating the subject depth direction position of the boundary B itself. For example, the information may be x (a distance from a position of an optical axis at an emitting end of the light emitting portion 40 to a central axis of the vibrator array 20), y (a distance from the position of the optical axis at the emitting end of the light emitting portion 40 to an abutment plane S1), or θ (an angle formed by the abutment plane S1 and an optical axis of the measurement light) as illustrated in FIG. 11. In a case where x, y, and θ are obtained, the distance W1 between the light emitting portion 40 and the vibrator array 20 can be obtained, and the subject depth direction position of the boundary B can also be obtained from the distance W1.

Further, in a case where the optical axis at the emitting end of the light emitting portion 40 is inclined with respect to the abutment plane, a "distance between the arrival region on the abutment plane of the measurement light and the acoustic wave detection portion" can be defined as follows. For example, in a case where nothing is mounted on the detection surface as illustrated in FIG. 11, an intersection between the detection surface and a central axis of the vibrator array 20 is defined as P1, and a maximum point in a case where an energy profile EP in the arrival region of the measurement light is approximated to a Gaussian distribution is defined as P2. In this case, the point P1 is a distal end of the probe through which the abutment plane passes. A distance W2 between the point P1 and the point P2 can be defined as the "distance between the arrival region and the acoustic wave detection portion".

Further, in a case where the operator confirms the display of the artifact non-generation region R1 and the artifact generation region R2 determined on the basis of the above-described correspondence table or calculation equation on the display unit 14, and appropriate region division can be considered from that, the operator may input information for designating the boundary B of the region division from the input unit 15 to reset the artifact non-generation region R1 and the artifact generation region R2.

Figure 6:
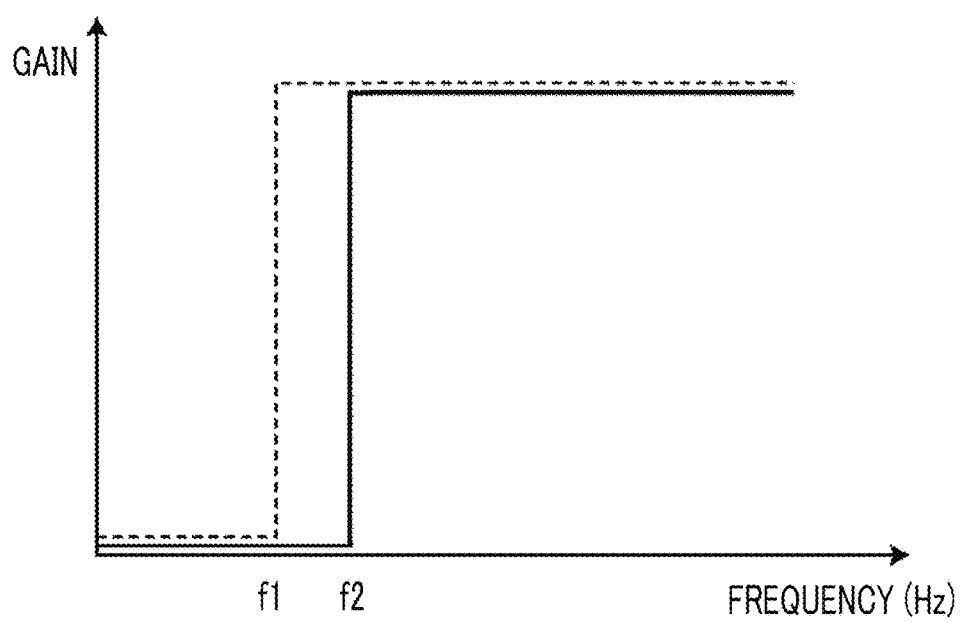
FIG. 6 is a schematic diagram illustrating another example of the pass characteristics of a filter.

The signal components in the low frequency range of the first photoacoustic wave detection signal and the second photoacoustic wave detection signal may be removed using a high pass filter, instead of removing the signal components in the low frequency range of the first photoacoustic wave detection signal and the second photoacoustic wave detection signal through the above-described band pass filtering process. FIG. 6 illustrates an example of basic pass characteristics of such a high pass filter. In FIG. 6, a broken line indicates pass characteristics of a first high pass filtering process (a first filtering process in the present invention) for the first photoacoustic wave detection signal, and a solid line indicates pass characteristics of a second high pass filtering process (a second filtering process in the present invention) for the second photoacoustic wave detection signal. That is, in this case, a cutoff frequency f2 for the second photoacoustic wave detection signal is set to be on a higher frequency side than a cutoff frequency f1 for the first photoacoustic wave detection signal.

For example, the cutoff frequency f1 is about 1 MHz and the cutoff frequency f2 is about 2 MHz. Thus, in this case, in a case where more signal components in the low frequency range of the second photoacoustic wave detection signal are removed as compared with the first photoacoustic wave detection signal, basically the same effects as in a case where the band pass filter having the pass characteristics illustrated in FIG. 5 is used can be obtained.

Figure 7:
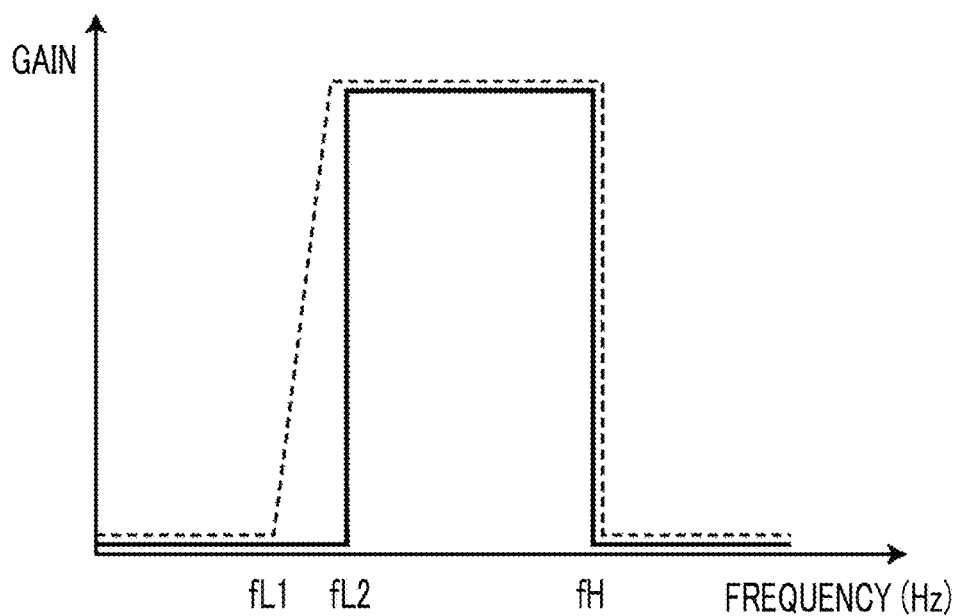
FIG. 7 is a schematic diagram illustrating yet another example of the pass characteristics of the filter.
Figure 8:
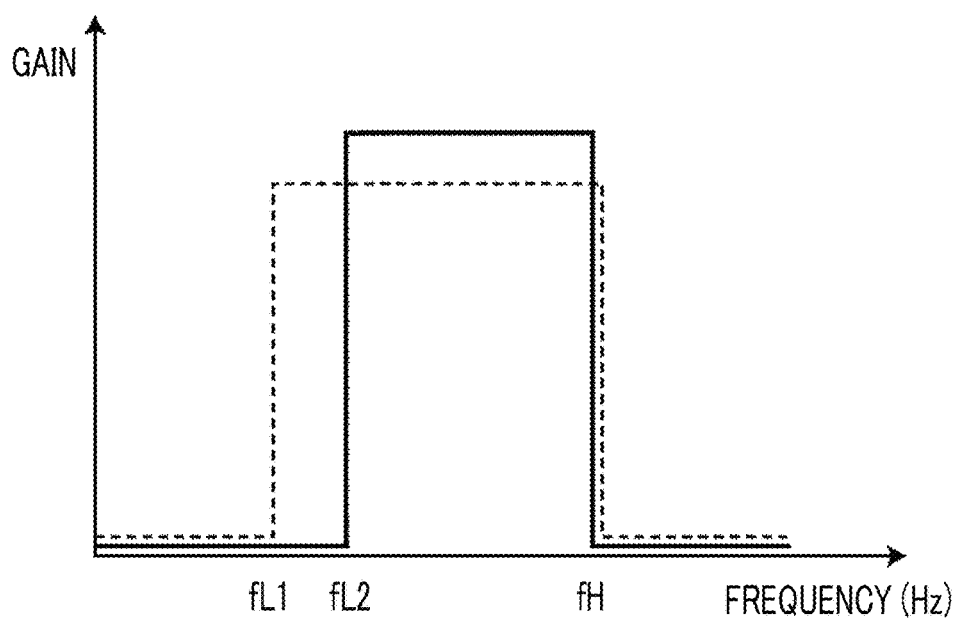
FIG. 8 is a schematic diagram illustrating yet another example of the pass characteristics of the filter.

Further, in a case where the band pass filter is used, a band pass filter having pass characteristics illustrated in FIG. 7 or pass characteristics illustrated in FIG. 8 can also be applied. In these figures, a broken line indicates pass characteristics of the first band pass filtering process for the first photoacoustic wave detection signal, and a solid line indicates pass characteristics of the second band pass filtering process for the second photoacoustic wave detection signal.

The pass characteristics illustrated in FIG. 7 differs from the pass characteristics illustrated in FIG. 5 in that a cutoff frequency on the low frequency side for the first photoacoustic wave detection signal is between fL1 and fL2 and continuously changes in a roll-off state. Further, in this case, since more signal components in the low frequency range of the second photoacoustic wave detection signal can be removed as compared with the first photoacoustic wave detection signal, basically the same effects as a case where the band pass filter having the pass characteristics illustrated in FIG. 5 is used can be obtained.

Although the cutoff frequency on the low frequency side of the first band pass filtering process for the first photoacoustic wave detection signal continuously changes between fL1 and fL2 in the example illustrated in FIG. 7, this cutoff frequency may change in a stepwise manner between fL1 and fL2.

The pass characteristics illustrated in FIG. 8 is different from the pass characteristics illustrated in FIG. 5 in that a filtering gain for the second photoacoustic wave detection signal is set to be higher than the filtering gain for the first photoacoustic wave detection signal. Further, in this case, since more signal components in the low frequency range of the second photoacoustic wave detection signal can be removed as compared with the first photoacoustic wave detection signal, basically the same effects as the case where the band pass filter having the pass characteristics illustrated in FIG. 5 is used can be obtained. Further, in this case, by removing more signal components in the low frequency range of the second photoacoustic wave detection signal, the amount by which overall signal intensity of the second photoacoustic wave detection signal is reduced can be compensated by increasing the filtering gain for the second photoacoustic wave detection signal as described above.

As described above, in a case where characteristics of filtering for the photoacoustic wave detection signal corresponding to a photoacoustic image of the artifact non-generation region R1 and characteristics of filtering for the photoacoustic wave detection signal corresponding to a photoacoustic image of the artifact generation region R2 are different from each other, frequency characteristics of the image easily rapidly changes at the boundary B between the artifact non-generation region R1 and the artifact generation region R2 in the photoacoustic image created and displayed on the basis of the photoacoustic wave detection signal after filtering. Hereinafter, an embodiment in which this abrupt change in the frequency characteristics is suppressed will be described.

A process to be described below is performed in the photoacoustic image generation unit 24 in FIG. 1, for example. In this embodiment, for example, two boundary regions BR1 and BR2 are set in a range including the boundary B between the artifact non-generation region R1 and the artifact generation region R2 schematically illustrated in FIG. 9. In this example, the boundary region BR1 belongs to the artifact non-generation region R1, and the boundary region BR2 belongs to the artifact generation region R2. In this case, the band pass filtering process is performed on the photoacoustic wave detection signals corresponding to the respective photoacoustic images in the boundary region BR1 and the boundary region BR2 by the band pass filter described above, but the band pass filtering process is a boundary region band pass filtering process which is different from the first band pass filtering process for the first photoacoustic wave detection signal corresponding to the photoacoustic image of the artifact non-generation region R1 and the second band pass filtering process for the second photoacoustic wave detection signal corresponding to the photoacoustic image in the artifact generation region R2.

Figure 10:
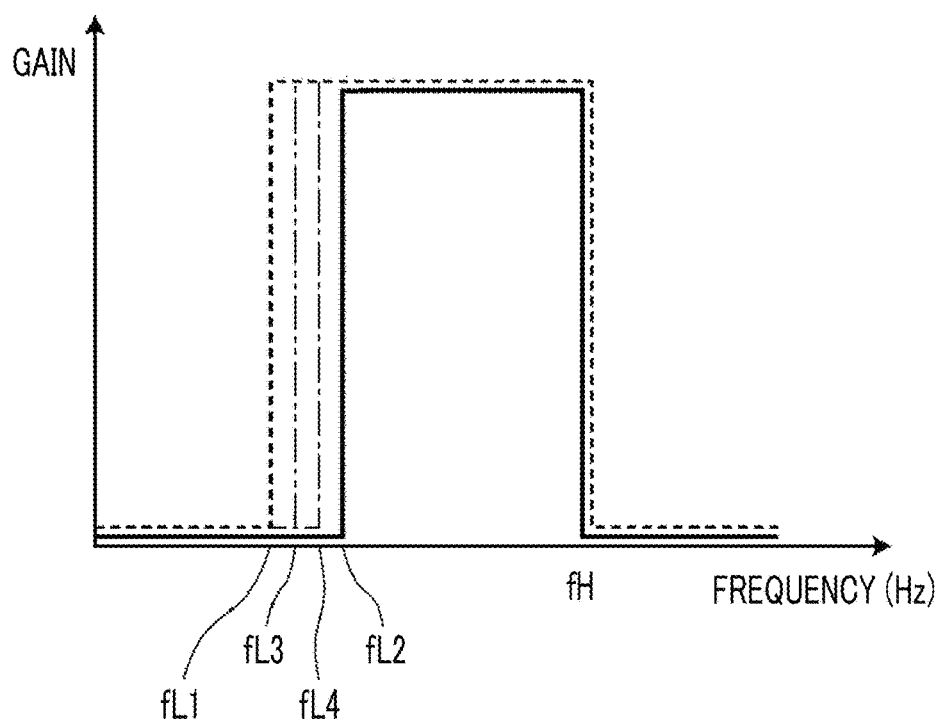
FIG. 10 is a schematic diagram illustrating yet another example of the pass characteristics of the filter

Here, the basic pass characteristics in each band pass filtering are illustrated in FIG. 10. In FIG. 10, a broken line indicates pass characteristics for the first photoacoustic wave detection signal, a solid line indicates pass characteristics for the second photoacoustic wave detection signal, a two-dot chain line indicates pass characteristic for the photoacoustic wave detection signal corresponding to the photoacoustic image of the boundary region BR1, and a one-dot chain line indicates pass characteristics for the photoacoustic wave detection signal corresponding to the photoacoustic image of the boundary region BR2.

As described above, the boundary region band pass filtering process for the photoacoustic wave detection signal corresponding to the photoacoustic image of the boundary region BR1 and the boundary region band pass filtering process for the photoacoustic wave detection signal corresponding to the photoacoustic image of the boundary region BR2 are intermediate processes between a first band pass filtering process for the first photoacoustic wave detection signal corresponding to the photoacoustic image of the artifact non-generation region R1 and a second band pass filtering process for the second photoacoustic wave detection signal corresponding to the photoacoustic image in the artifact generation region R2.

More specifically, a cutoff frequency fL3 (=1.3 MHz) on the low frequency side which is one of the pass characteristics of the band filtering process for the boundary region BR1, and a cutoff frequency fL4 (=1.7 MHz) on the low frequency side of the band filtering process for the boundary region BR2 are determined according to the subject depth direction positions of the boundary region BR1 and the boundary region BR2 on the basis of the cutoff frequency fL1 (=1 MHz) on the low frequency side of the first band pass filtering process for the artifact non-generation region R1 and the cutoff frequency fL2 (=2 MHz) on the low frequency side of the second band pass filtering process for the artifact generation region R2.

As described above, by setting the cutoff frequencies fL1 to fL4 on the low frequency side of the respective band pass filtering processes, the frequency characteristics of the photoacoustic image do not abruptly change at the boundary B between the artifact non-generation region R1 and the artifact generation region R2. That is, in the photoacoustic image displayed on the display unit 14, the frequency characteristics gradually change at each boundary of the artifact non-generation region R1, the boundary region BR1, the boundary region BR2, and the artifact generation region R2, and diagnostic performance of the photoacoustic image is enhanced.

Although the two boundary regions BR1 and BR2 are set in the range including the boundary B between the artifact non-generation region R1 and the artifact generation region R2 in the embodiment described above, one or more boundary regions may be set. In a case where only one boundary region is set, an edge of the boundary region may be aligned with the boundary B. The more the boundary regions are set, the smoother the change in the frequency characteristics at the boundary of each region, but a time required for the filtering process correspondingly increases. Therefore, the appropriate number of boundary regions may be set in consideration of both of the respects.

Next, another embodiment of the present invention in which it is possible to suppress a sudden change in frequency characteristics of the image at the boundary B between the artifact non-generation region R1 and the artifact generation region R2 will be described. A process to be described below is performed in the photoacoustic image generation unit 24 in FIG. 1, for example.

Figure 9:
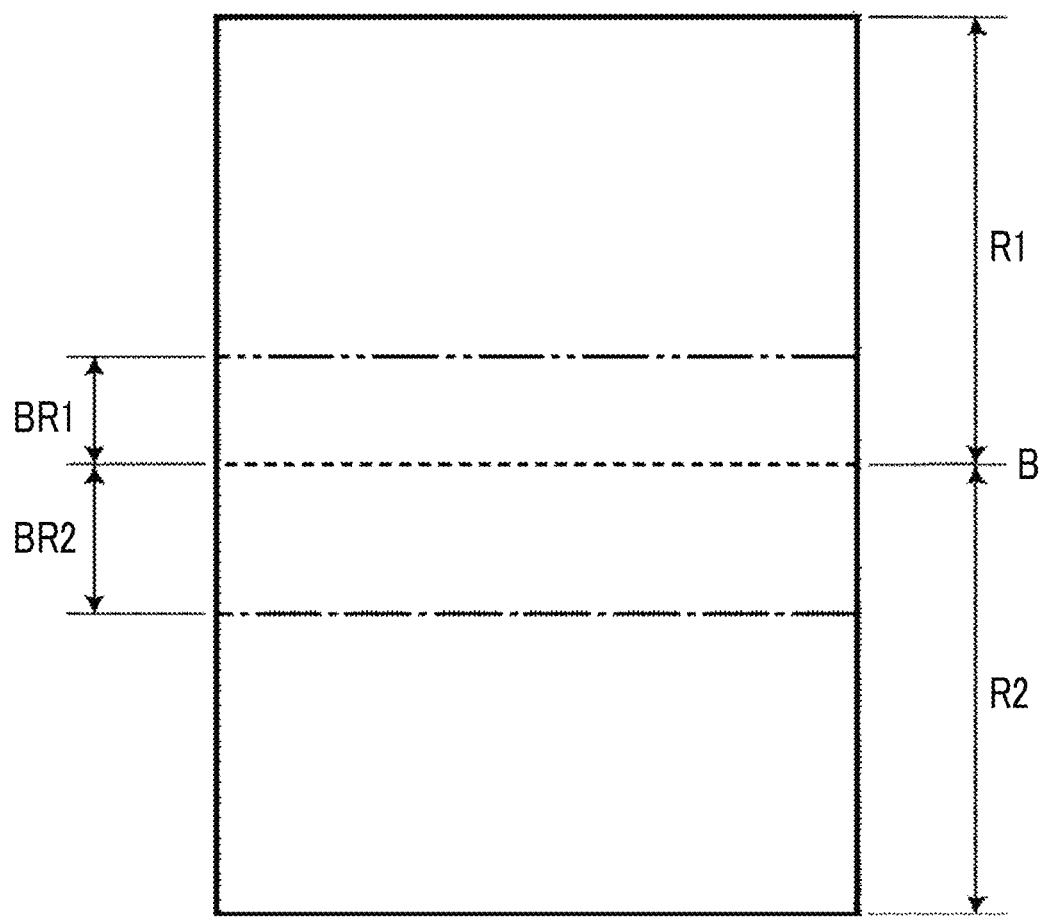
FIG. 9 is a schematic diagram illustrating a boundary region.

In this embodiment, at least one boundary region is set in a range including the boundary between the artifact non-generation region R1 and the artifact generation region R2, as illustrated in FIG. 9. In the embodiment, two boundary regions BR1 and BR2 are set, as in the example of FIG. 9. A first band pass filtering process in which the cutoff frequency fL1 on the low frequency side is set to 1 MHz is performed on the first photoacoustic wave detection signal corresponding to the photoacoustic image of the artifact non-generation region R1 to obtain a first processed photoacoustic wave detection signal. On the other hand, a second band pass filtering process in which the cutoff frequency fL2 on the low frequency side is set to 2 MHz is performed on the second photoacoustic wave detection signal corresponding to the photoacoustic image of the artifact generation region R2 to obtain a second processed photoacoustic wave detection signal.

Weighted addition is performed on the first processed photoacoustic wave detection signal and the second processed photoacoustic wave detection signal according to the subject depth direction position of the boundary region BR1 and the boundary region BR2 to obtain a photoacoustic wave detection signal for the boundary region BR1 and a photoacoustic wave detection signal for the boundary region BR2. In this case, for example, the weighted addition is performed by giving a weighting coefficient of 0.7 to the first processed photoacoustic wave detection signal and a weighting coefficient of 0.3 to the second processed photoacoustic wave detection signal to obtain the photoacoustic wave detection signal for boundary region BR1. Further, for example, the weighted addition is performed by giving a weighting coefficient of 0.3 to the first processed photoacoustic wave detection signal and a weighting coefficient of 0.7 to the second processed photoacoustic wave detection signal to obtain the photoacoustic wave detection signal for boundary region BR2.

The photoacoustic image of the boundary region BR1 is generated using the photoacoustic wave detection signal for the boundary region BR1 obtained as described above, the photoacoustic image of the boundary region BR2 is generated using the photoacoustic wave detection signal for the boundary region BR2, the photoacoustic image is generated using the first processed photoacoustic wave detection signal for a portion other than the boundary region BR1 of the artifact non-generation region R1, the photoacoustic image is generated using the second processed photoacoustic wave detection signal for a portion other than the boundary region BR2 of the artifact generation region R2, and the photoacoustic images are combined to generate and display one photoacoustic image.

In the photoacoustic image displayed on the display unit 14 in this way, the frequency characteristics gradually change at each boundary of the artifact non-generation region R1, the boundary region BR1, the boundary region BR2, and the artifact generation region R2, and diagnostic performance of the photoacoustic image is enhanced.

Further, in the embodiment, since the sudden change in the frequency characteristics is suppressed, the embodiment is superior to the case where the characteristics of the filtering processes for the respective photoacoustic wave detection signals of the artifact non-generation region R1, the artifact generation region R2, the boundary region BR1, and the boundary region BR2 are changed as described above in that a calculation process is light.

Figure 12:
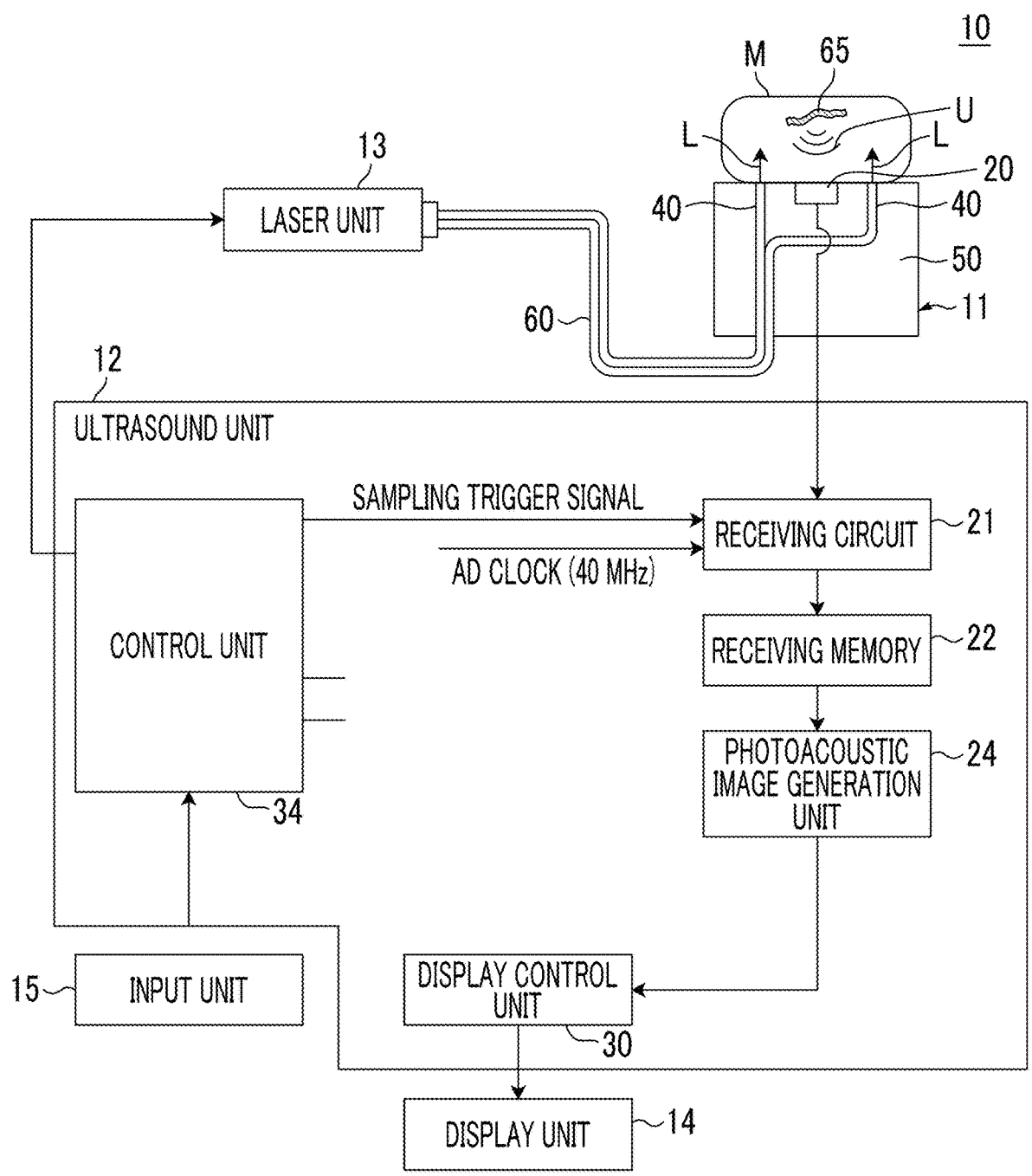
FIG. 12 is a schematic diagram illustrating an overall configuration of a photoacoustic measurement device according to another embodiment of the present invention.

Although the photoacoustic measurement device 10 capable of generating and displaying the reflected ultrasonic image together with the photoacoustic image has been described above, it is to be understood that the present invention is applied to a photoacoustic measurement device configured to perform only the generation and the display of the photoacoustic image without performing the generation and the display of the reflected ultrasonic image. FIG. 12 illustrates an example of the photoacoustic measurement device 10 configured in this way. The photoacoustic measurement device 10 illustrated in FIG. 12 is of a form in which the data separation means 23, the ultrasonic image generation unit 29, and the transmission control circuit 33 are excluded, unlike the photoacoustic measurement device 10 illustrated in FIG. 1.

What is claimed is:

1. A photoacoustic measurement device comprising:
a probe including a light guide that emits measurement light to a subject, and an acoustic wave detector that is arranged in parallel to the light guide and detects photoacoustic waves generated in the subject due to emission of the measurement light, and
a processor configured to:
generate a photoacoustic image on the basis of a photoacoustic wave detection signal output by the acoustic wave detector;
discriminate an artifact generation region and an artifact non-generation region in the photoacoustic image on the basis of at least a positional relationship between the light guide and the acoustic wave detector; and
perform a first filtering process on a first photoacoustic wave detection signal corresponding to a photoacoustic image of the artifact non-generation region among the photoacoustic wave detection signals, and perform a second filtering process on a second photoacoustic wave detection signal corresponding to a photoacoustic image of the artifact generation region among the photoacoustic wave detection signals,
wherein the second filtering process includes further reducing the photoacoustic wave detection signal in a frequency range lower than a predetermined frequency as compared with the first filtering process,
wherein the first filtering process includes a first band pass filtering process and the second filtering process includes a second band pass filtering process, and
wherein a cutoff frequency on a low frequency side in the second band pass filtering process is set to be on a higher frequency side as compared with a cutoff frequency on a lower frequency side in the first band pass filtering process, and a cutoff frequency on a high frequency side in the second band pass filtering process is set to be the same as a cutoff frequency on a high frequency side in the first band pass filtering process.

2. The photoacoustic measurement device according to claim 1,
wherein the processor is further configured to discriminate the artifact generation region and the artifact non-generation region on the basis of a correspondence table in which a positional relationship between the light guide and the acoustic wave detector is associated with a boundary between the artifact generation region and the artifact non-generation region.

3. The photoacoustic measurement device according to claim 1,
wherein the processor is further configured to discriminate the artifact generation region and the artifact non-generation region using a calculation equation for calculating a boundary between the artifact generation region and the artifact non-generation region from a positional relationship between the light guide and the acoustic wave detector.

4. The photoacoustic measurement device according to claim 1,
wherein the processor is further configured to correct the discrimination according to a sound speed at a portion of a subject through which the photoacoustic waves propagate.

5. The photoacoustic measurement device according to claim 1,
wherein the processor is further configured to perform a boundary region filtering process different from the first filtering process and the second filtering process on a photoacoustic wave detection signal corresponding to a photoacoustic image of at least one boundary region set in a range including a boundary between the artifact non-generation region and the artifact generation region.

6. The photoacoustic measurement device according to claim 5,
wherein the boundary region filtering process is an intermediate filtering process between the first filtering process and the second filtering process.

7. The photoacoustic measurement device according to claim 6,
wherein pass characteristics of the boundary region filtering process is determined according to a subject depth direction position of the boundary region on the basis of pass characteristics of the first filtering process and pass characteristics of the second filtering process.

8. The photoacoustic measurement device according to claim 1,
wherein an image corresponding to a photoacoustic image of at least one boundary region set in a range including a boundary between the artifact non-generation region and the artifact generation region is formed using a signal obtained by performing weighted adding on the first photoacoustic wave detection signal subjected to the first filtering process and the second photoacoustic wave detection signal subjected to the second filtering process according to a subject depth direction position of the boundary region.

9. A signal processing method of a photoacoustic measurement device comprising a probe including a light guide that emits measurement light to a subject, and an acoustic wave detector that is arranged in parallel to the light guide and detects photoacoustic waves generated in the subject due to emission of the measurement light, and a processor configured to generate a photoacoustic image on the basis of a photoacoustic wave detection signal output by the acoustic wave detector, the signal processing method comprising:
discriminating an artifact generation region and an artifact non-generation region in the photoacoustic image on the basis of at least a positional relationship between the light guide and the acoustic wave detector;
performing a band pass filtering process including a first filtering process on a first photoacoustic wave detection signal corresponding to a photoacoustic image of the artifact non-generation region among the photoacoustic wave detection signals and
a second filtering process on a second photoacoustic wave detection signal corresponding to a photoacoustic image of the artifact generation region among the photoacoustic wave detection signals; and
further reducing the photoacoustic wave detection signal in a frequency range lower than a predetermined frequency in the second filtering process as compared with the first filtering process,
wherein a cutoff frequency on a low frequency side in the second filtering process is set to be on a higher frequency side as compared with a cutoff frequency on a lower frequency side in the first filtering process, and a cutoff frequency on a high frequency side in the second filtering process is set to be the same as a cutoff frequency on a high frequency side in the first filtering process.

10. The signal processing method of a photoacoustic measurement device according to claim 9,
wherein the artifact generation region and the artifact non-generation region are discriminated on the basis of a correspondence table in which a positional relationship between the light guide and the acoustic wave detector is associated with a boundary between the artifact generation region and the artifact non-generation region.

11. The signal processing method of a photoacoustic measurement device according to claim 9,
wherein the artifact generation region and the artifact non-generation region are discriminated using a calculation equation for calculating a boundary between the artifact generation region and the artifact non-generation region from a positional relationship between the light guide and the acoustic wave detector.

12. The signal processing method of a photoacoustic measurement device according to claim 9,
wherein the discrimination is corrected according to a sound speed at a portion of a subject through which the photoacoustic waves propagate.

13. The signal processing method of a photoacoustic measurement device according to claim 9,
wherein a boundary region filtering process different from the first filtering process and the second filtering process is performed on a photoacoustic wave detection signal corresponding to a photoacoustic image of at least one boundary region set in a range including a boundary between the artifact non-generation region and the artifact generation region.

14. The signal processing method of a photoacoustic measurement device according to claim 13,
wherein the boundary region filtering process is an intermediate filtering process between the first filtering process and the second filtering process.

15. The signal processing method of a photoacoustic measurement device according to claim 14,
wherein pass characteristics of the boundary region filtering process is determined according to a subject depth direction position of the boundary region on the basis of pass characteristics of the first filtering process and pass characteristics of the second filtering process.

16. The signal processing method of a photoacoustic measurement device according to claim 9, further comprising:
forming an image corresponding to a photoacoustic image of at least one boundary region set in a range including a boundary between the artifact non-generation region and the artifact generation region using a signal obtained by performing weighted adding on the first photoacoustic wave detection signal subjected to the first filtering process and the second photoacoustic wave detection signal subjected to the second filtering process according to a subject depth direction position of the boundary region.

* * * * *